United States Patent [19]

Sim et al.

[11] Patent Number: 5,354,861
[45] Date of Patent: Oct. 11, 1994

[54] 2-(BENZYL)-3-ARYLBENZOFURANS AS ANTITUMOUR AND HYPOCHOLESTEROLEMIC AGENTS

[75] Inventors: Keng-Yeow Sim; Oi-Lian Kon; Chin-Chin Teo; Siu-Choon Ng; Srikanth Natarajan, all of Singapore, Singapore

[73] Assignee: National University of Singapore, Singapore, Singapore

[21] Appl. No.: 971,507

[22] Filed: Nov. 4, 1992

[51] Int. Cl.$^5$ ............... C07D 413/10; C07D 405/10; C07D 307.80
[52] U.S. Cl. ................... 544/153; 546/196; 548/525; 549/467
[58] Field of Search ............ 548/525; 546/196; 544/153; 549/467

[56] References Cited

U.S. PATENT DOCUMENTS 4,075,227  2/1978  Jones et al. ............. 260/330.5
4,536,516  8/1985  Harper et al. ............ 514/514

FOREIGN PATENT DOCUMENTS 1013907  12/1965  United Kingdom .

OTHER PUBLICATIONS

Bloom and fishman, Cancer (1983), vol. 51, pp. 1190–1194.
Faye et al., Proc. Natl. Acad. Sc. U.S.A. (1983), vol. 80, pp. 3158–3162.
Geissman and Hinreiner, J. Am. Chem. Soc. (1951), vol. 73, pp. 782–786.
Teo et al., J. Med. Chem., 1992, vol. 35, pp. 1330–1339.
Ho et al., J. Exp. med. (1977), vol. 145, pp. 1531–1549.
Jones et al. J. Med. Chem. (1979), vol. 22, pp. 962–966.
Jones et al., J. Med. Chem. (1984), vol. 27, pp. 1057–1066.
Kon, J. Biol. Chem. (1983), vol. 258, pp. 3173–3177.
Sutherland et al., Biochem. Biophys. Res. Commun. (1986), vol. 140, pp. 523–529.
Reddel et al., Cancer Res. (1985), vol. 45, pp. 1525–1531.

*Primary Examiner*—Johann Richter
*Assistant Examiner*—Michael B. Hydorn
*Attorney, Agent, or Firm*—Lowe, Price, LeBlanc & Becker

[57] ABSTRACT

The synthesis and the biological evaluation of a series of basic ethers of 2-benzyl-3-arylbenzofurans as antitumor agents is described. These compounds bind significantly to the antiestrogen-binding sites but only poorly to the estrogen receptor sites and are cytotoxic to tumor cells. Some of these compounds also significantly inhibited de novo cholesterol biosynthesis in an estrogen receptor negative lymphoma cell line rich in antiestrogen-binding sites.

10 Claims, 2 Drawing Sheets

FIG. 1(A)
FIG. 1(B)
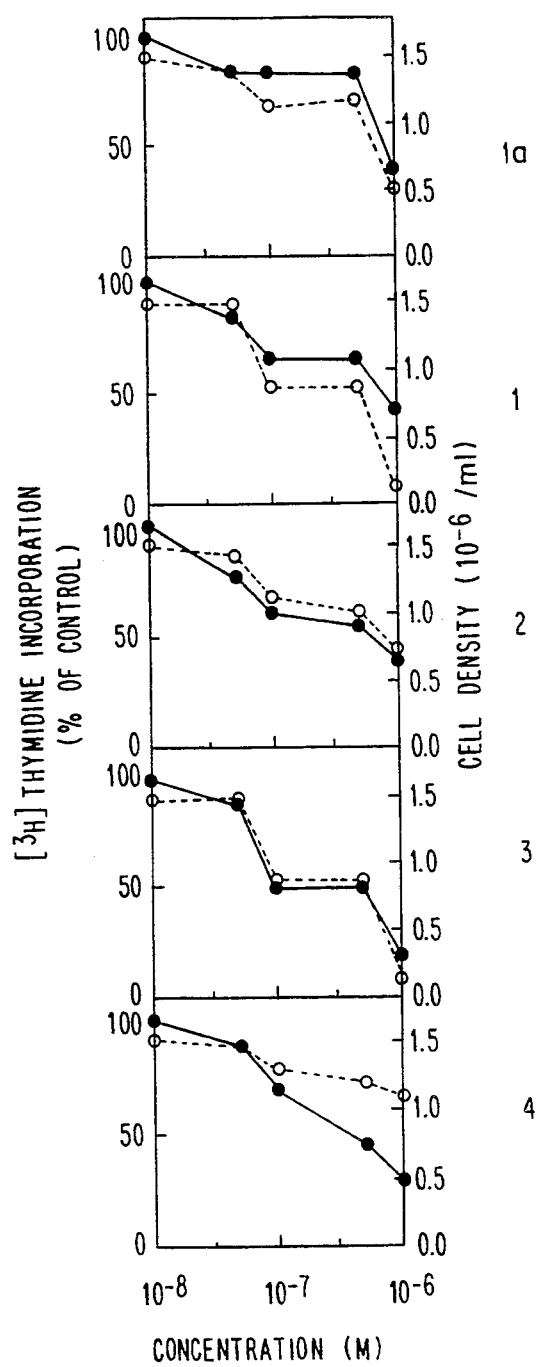
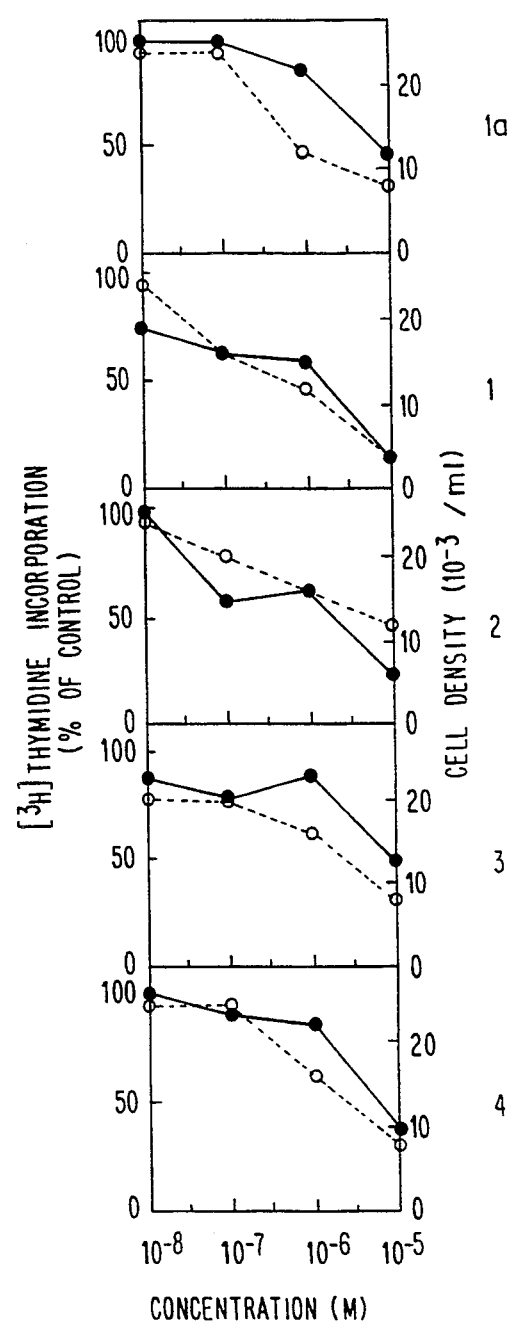

2-(BENZYL)-3-ARYLBENZOFURANS AS ANTITUMOUR AND HYPOCHOLESTEROLEMIC AGENTS

BACKGROUND OF THE INVENTION

1. Field of the Invention

This invention relates to basic ethers of 2-benzyl-3-arylbenzofurans, their preparation and use in therapy as antitumour and hypocholesterolemic agents.

2. Description of prior art

A class of triarylethylene derivatives known as the nonsteroidal antiestrogens are now widely used in the treatment of human breast cancer. Their discovery as biological antagonists of estrogen action in the 1950s suggested possible usefulness in the treatment of estrogen responsive diseases. While several such compounds were initially investigated as potential drugs, only tamoxifen, 1-[4-(2-dimethylaminoethoxy)phenyl]-1,2-diphenylbut1-(Z)-ene (Harper et at., U.S. Pat. No. 1,013,907), was approved in the 1970s for the treatment of estrogen receptor (ER)-positive human breast carcinoma on the basis of extensive clinical trials which established its efficacy and low incidence of adverse side effects. Tamoxifen is now the drug of choice for endocrine treatment of all stages of breast cancer in pre- and postmenopausal patients whose tumours are ER-positive. Nonisomerizable antiestrogens such as trioxifene (Jones et al., *J.Med.Chem.* (1979) 22:962–966) and the benzothiophene antiestrogens (Jones et al., *J.Med.-Chem.* (1984) 27:1057–1066), LY117018 and LY156758, are examples of agents subsequently developed in attempts to improve upon the actions of tamoxifen. Trioxifene, although an effective antiestrogen in clinical trials, possesses greater estrogenic activity than tamoxifen a property that can be expected to reduce its efficacy in estrogen-responsive tumours. The benzothiophene compounds are partial antagonists/agonists (like tamoxifen) but characterized by a shorter duration of action in vivo, a practical disadvantage possibly due to their hydroxylated nature.

The precise mechanism(s) of action of nonsteroidal antiestrogens is not entirely understood although it is clear that a substantial part of their activity depends on the ability of these drugs to interact with the estrogen receptor.

The following well-documented observations however indicate that binding to the estrogen receptor is not the only means by which antiestrogens express biological activity: (1) Antiestrogens also inhibit the proliferation of cells which lack the receptor (Reddel et al., *Cancer Res.*(1985), 45:1525–1531). (2) Antiestrogen-resistance supervenes clinically, often without any change in the ER status of the resistant tumour (Bloom and Fishman *Cancer* (1983) 51:1190–1194). (3) Some antiestrogen effects cannot be reversed or prevented by co-administration of estrogen (Sutherland et al., *Biochem. Biophys. Res. Commun.* (1986) 140:523–529).

More recently, a second high-affinity binding site for antiestrogens distinct from the estrogen receptor has been identified. This intracellular antiestrogen-binding site (AEBS) is present in all mammalian tissues and cell lines thus far examined, including normal human tissues, breast carcinoma and other human tumours and in breast cancer cell lines (Kon, *J.Biol. Chem.*(1983) 258:3173–3177).

SUMMARY OF THE INVENTION

The novel compounds of the present invention may be presented by the formula

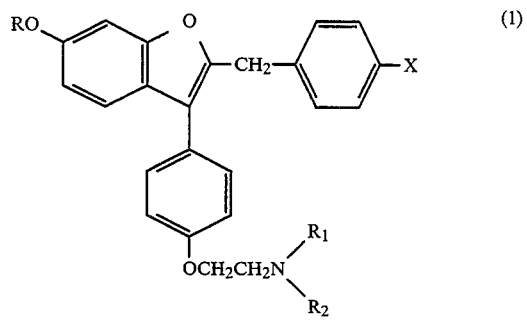

wherein

R represents H, or methyl group, $R_1$, $R_2$ are identical or different and represent $C_{1-2}$ alkyl, especially methyl or ethyl groups or $R_1$,$R_2$, together with the nitrogen atom to which they are attached represent a saturated heterocyclic group, especially a pyrrolidino-, piperidino- or morpholino- group, and their pharmaceutically acceptable acid addition salts and X represents bromo-, chloro- ,fluoro- or hydrogen group.

The benzofuran derivatives of this invention and their acid addition salts may be useful for the control of tumours and may also have useful hypocholesterolemic activity.

BRIEF DESCRIPTION OF THE FIGURES

FIG. 1 shows the effect of tamoxifen (1a), benzofurans (1-4) on [$^3$H]thymidine incorporation (closed circles) and cell density (open circles) of (A) EL4 cells and (B) MCF7 cells, after 48 hours of treatment with test compounds. Concentration are shown on the x-axis.

DETAILED DESCRIPTION OF THE INVENTION

Figure 2:
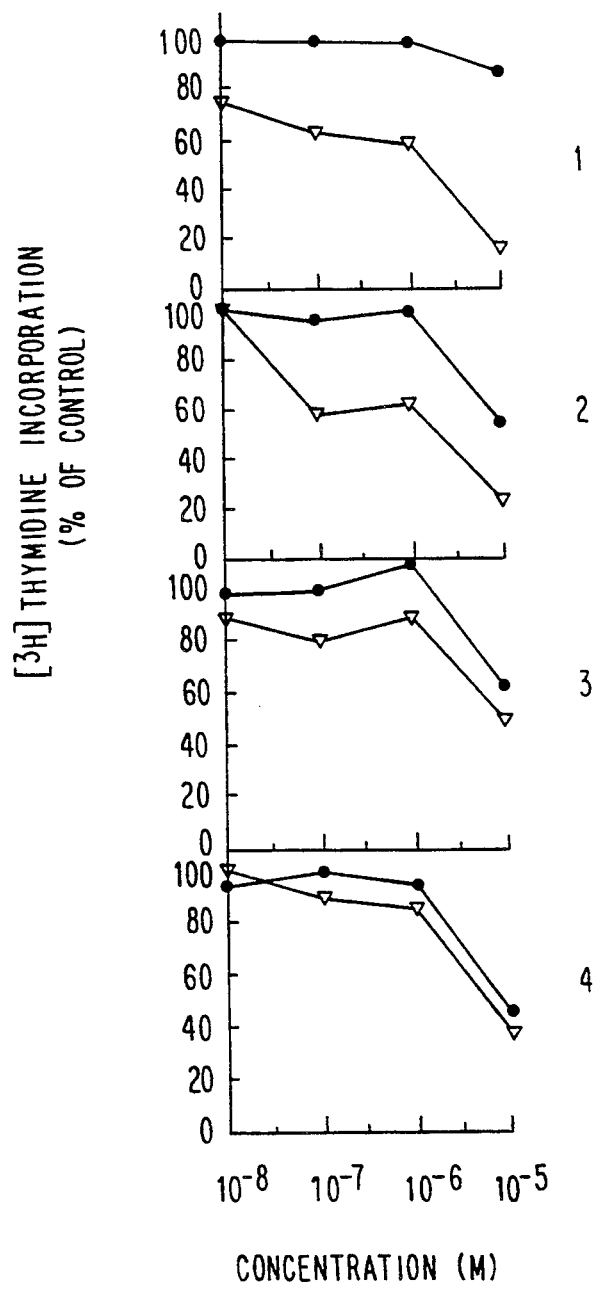
FIG. 2 shows the effect of benzofurans (1-4) on [$^3$H]thymidine incorporation by MCF7 (open triangles) and RTx6 cells (closed circles), after 48 hours of treatment with test compounds. Concentrations are shown on the x-axis.

We have found two suitable methods of manufacturing the compounds of the above formula (I). The first approach comprises reacting 2-benzylbenzofuranone having the formula (II)

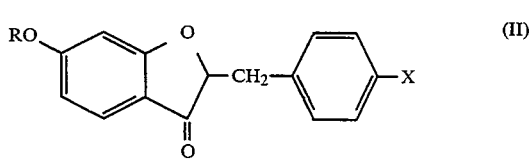

with aryllithium bromide (or arylmagnesium bromide) having the formula (HI),

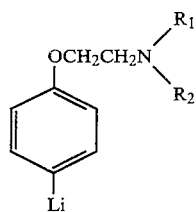
(III)

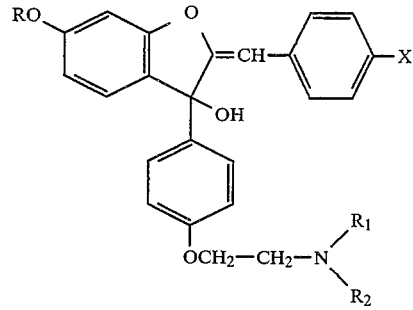
(V)

The reaction is advantageously carried out in an unreactive solvent medium. Some suitable solvents for this purpose are tetrahydrofuran and ether. This is followed by hydrolysis of the reaction product by heating with hydrochloric acid in ethanol for 3 hours at reflux, where R,$R_1$, $R_2$, X are as previously defined.

The product of the reaction can be isolated directly as the hydrochloride salt; following basification, as the free base; or following basification and subsequent salt formation, as an acid-addition salt.

On the other hand, if it is desired to obtain the alkanol compound from this reaction, prolonged treatment with mineral acid should be avoided. In any particular case, the identity of the reaction product as the alkanol compound or the alkene compound can be conveniently determined by examining the infrared absorption spectrum for absorption due to a hydroxyl group. Strong hydroxyl absorption indicates that the product is the alkanol compound, whereas absence of such absorption indicates that dehydration has occurred, and the product is the alkene compound. Weak hydroxyl absorption indicates that a mixture of the two has been formed.

The benzofuranone compounds having formula (II) above are prepared by hydrogenation of the corresponding protected benzylidenes (aurones) having the formula (IV)

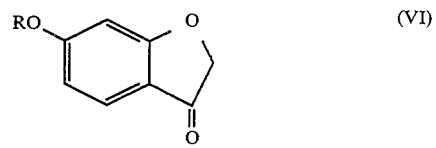
(IV)

in the presence of palladium or platinium oxide at room temperature where R, X has the same meaning as previously given. Suitable solvents for the reaction include alcohols and ethyl acetate. The reaction is substantially completed after a period which may vary from 30 minutes to 2 hours. The product obtained is non-fluorescent.

The second approach of synthesising compounds of formula (I) involves the reaction of benzylidenedihydrobenzofuranols of formula (V), where R, $R_1$, $R_2$ and X are as previously defined, with magnesium bromide etherate, followed by treatment with lithium aluminium hydride. This method gives better yields. The benzylidenedihydrobenzofuranols can be prepared in good yields by treatment of the benzylidene compounds having formula (IV) with the aryllithium bromide (or arylmagnesium bromide) having the formula (III).

The benzylidene compounds having formula (IV) above that are required as starting materials in the foregoing processes are synthesised (Geissman and Hinreiner, *J.Am.Chem.Soc.*(1951),73:782–786) by condensing the appropriate aldehydes with benzofuranone having the formula (VI)

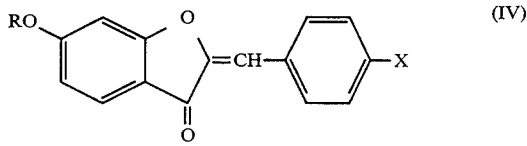
(VI)

where R has the aforementioned significance in catalytic amount of concentrated hydrochloric acid.

The compounds of the invention are new chemical compounds that may be useful pharmacological agents exhibiting antitumour, and hypocholesterolemic activity.

The following examples are intended to illustrate the invention described herein without unduly restricting it. Examples 1–5 illustrate preparation of chloro- derivatives. Examples 6–9 illustrate preparation of fluoro- derivatives. Examples 10, 11, 12 indicate ligand binding, antiproliferative effects and cholesterol biosynthesis. Example 13 indicates pharmaceutical composition.

EXAMPLE 1

2-(p-Chlorobenzyl-3-[p-(2-dimethylaminoethoxy)-phenyl]-6-methoxybenzo[b]furan ( 1 )

n-Butyl lithium (5.27 ml, 7.80 mmole) in THF was added dropwise to a solution of 4-[2-dimethylaminoethoxy]phenyl bromide (1.90 g, 7.80 mmol) in THF (5 ml) at −78° C. After stirring for 30 minutes at −78° C., 2-(p-chlorobenzyl)-6-methoxy-3(2H)benzofuranone (1.50 g, 5.20 mmol) in THF was added dropwise to the mixture at −78° C. The reaction mixture was stirred at −78° C. for 1 hour, and allowed to warm to room temperature. After stirring for 18 hours, it was quenched with saturated ammonium chloride and THF was evaporated off. The residue was dissolved in ethyl acetate (30 ml), washed with sodium chloride (2×20 ml), dried (anhydrous magnesium sulphate) and the solvent evaporated off to yield an oil which showed three spots on tlc. The oil was purified by flash chromatography (eluent,dichloromethane: hexane: triethylamine=1:1:0.2), yielding the tertiary alcohol (R$_f$=0.25) which gave a characteristic reddish stain with ammonium molybdate-cefic sulphate in 2M sulphuric acid spray. The alcohol without characterisation was dehydrated. A solution of methanol (0.40 ml) saturated with dry hydrogen chloride gas was added to the tertiary alcohol dissolved in sodium-dried ether (40 ml). A white precipitate was formed which was filtered and recrystallised from ethanol to give the hydrochloride salt of the title compound as a white crystalline solid. Yield (23 %); m.p. 208°-209° C; $^1$H-NMR (CDCl$_3$) δ2.96 (s, 6H, N(CH$_3$)$_2$), 3.48 (t, 2H, J 6.0 Hz OCH$_2$CH$_2$N), 3.85 (s, 3H, OCH$_3$),4.10 (s, 2H, CH$_2$ at C-2), 4.59 (t, 2H, J 6.0 Hz, OCH$_2$CH$_2$N), 6.81-7.45 (m, 11H, ArH ); m/z (%) 437 (M+HCl, 7), 435 (M+HCl, 23), 364 (12), 58 (100). (Found: C, 66.00, H, 5.46, N, 3.01, Cl, 15.01. C$_{26}$H$_{26}$ClNO$_3$.HCl required C, 66.10, H, 5.76, N, 2.96, Cl, 15.01).

EXAMPLE 2

2-(p-Chlorobenzyl)-3-[p-(2-pyrrolidinoethoxy)phenyl]-6-methoxybenzo[b]furan (2)

4-[2-Pyrrolidinoethoxy]phenyl bromide (1.41 g, 5.20 mmol) in dry THF (50 ml) was added to magnesium turnings (312 mg, 13.0 mmol) in a dry 3-necked round bottom flask under an oxygen-free nitrogen atmosphere and the mixture was maintained under gentle reflux. 1,2-Dibromoethane (0.22 ml, 2.60 mmol) was added dropwise over a period of ½ hour. The mixture was heated gently until the magnesium was nearly consumed (ca. ½ hour). 2-(p-Chlorobenzyl)-6-methoxy-3(2H)-benzofuranone (740 mg, 2.60 mmol) in THF (50 ml) was added dropwise to the mixture at 0° C. The reaction mixture was allowed to warm to room temperature and refluxed for 18 hours. The cooled mixture was quenched with saturated ammonium chloride (30 ml), extracted with dichloromethane (3×40 ml), washed with water, dried (anhydrous sodium sulphate) and the solvent evaporated off to yield an oil which was dehydrated with concentrated hydrochloric acid (2 ml) in ethanol (25 ml). The mixture was refluxed for 2 hours, whereupon ethanol was removed. It was then basified with 10% sodium hydroxide (20 ml) and extracted with dichloromethane (3×40 ml). The dichloromethane extract was washed with water (3×20 ml), dried (anhydrous sodium sulphate) and the solvent was evaporated off to give a solid which was chromatographed on silica gel. Elution with (dichlorothene: hexane: triethylamine=1:2:0.3), yielded a colourless solid which was recrystallised from methanol to give 2-(p-chlorobenzyl)-3-[p-(2-pyrrolidinoethoxy)phenyl]-6-methoxybenzo[b]furan (2), m.p. 75° C. Dry hydrogen chloride gas was bubbled through an ethereal solution of the free base for 10 minutes and cooled to 0° C. The hydrochloride salt which precipitated out was filtered off at the pump, rinsed with ether, and recrystallised from isopropanol to yield white crystals of the hydrochloride salt. Yield (22%); m.p. 223°-225° C.; $^1$H-NMR (CDCl$_3$)δ 1.82 (m, 4H, N(CH$_2$CH$_2$)$_2$), 2.65 (br s, 4H, N(CH$_2$CH$_2$)$_2$), 2.93 (t, 2H, J6.0 Hz, OCH$_2$CH$_2$N), 3.84 (s, 3H, OCH$_3$), 4.16 (distorted t, 4H,J 6.0 Hz, OCH$_2$CH$_2$N, CH$_2$ at C-2), 6.80-7.47 (m, 11H, ArH ); m/z (%) 463 (M+−HCl, 28), 461 (M+−HCl, 10), 364 (17), 98 (38), 84 (100). (Found: C, 67.37, H, 5.92, N, 2.56, Cl, 13.95. C$_{28}$H$_{28}$ClNO$_3$.HCl required C, 67.47, H, 5.66, N, 2.81, Cl, 14.23).

EXAMPLE 3

2-(p-Chlorobenzyl)-3-[p-(2-piperidinoethoxy)phenyl]-6-methoxybenzo[b]furan (3)

n-Butyl lithium (5.27 ml, 7.80 mM) in THF was added dropwise to a solution of 4-[2-piperidinoethoxy]phenyl bromide (1.45 g, 7.80 mmol) in THF (5 ml) at −78° C. After stirring for 30 minutes at −78° C., 2-(p-chlorobenzyl)-6-methoxy-3(2H)- benzofuranone (1.50 g, 5.20 mmol) in THF was added dropwise to the mixture at −78° C. The reaction mixture was stirred at −78° C. for 1 hour. It was warmed to room temperature. After stirring for 18 hours, it was quenched with saturated ammonium chloride and THF was evaporated off. The residue was dissolved in ethyl acetate (30 ml), washed with sodium chloride (2×20 ml), dried (anhydrous magnesium sulphate) and the solvent evaporated off to yield an oil which was purified by flash chromatography (eluent, dichloromethane:hexane:triethylamine=1:1:0.2), yielding a light brown oil of the tertiary alcohol, 2-(p-chlorobenzyl)-3-[p-(2-piperidinoethoxy)phenyl]-6-methoxybenzofuranol (R$_f$=0.23) which gave a characteristic reddish stain with ammonium molybdate-ceric sulphate in 2M sulphuric acid spray. A solution of methanol (0.40 ml) saturated with dry hydrogen chloride gas was added to the tertiary alcohol dissolved in sodium-dried ether (40 ml). The reaction mixture was stirred at room temperature for ½ hour. A white precipitate was formed which was filtered and recrystallised from ethanol to give the hydrochloride salt of the title compound as a white crystalline solid. Yield (74 %); m.p. 133°-136° C.; $^1$H-NMR (CDCl$_3$)δ 1:58-3.03 (bm, 10H, N(CH$_2$CH$_2$)$_2$CH$_2$), 3.42 (t, 2H, J 6.0 Hz, OCH$_2$CH$_2$N), 3.85 (s, 3H, OCH$_3$), 4.10 (s, 2H, CH$_2$ at C-2), 4.44 (t, 2H, J 6.0 Hz, OCH$_2$CH$_2$N), 6.81-7.44 (m, 11H, ArH); m/z (%) 477 (M+−HCl, 8), 475 (M+−HCl, 3), 364 (13), 98 (100). (Found: C, 64.89, H, 6.20, N, 2.49, Cl, 13.38. C$_{29}$H$_{30}$O$_3$ClN.HCl.3/2H$_2$O required C, 64.56, H, 6.35, N, 2.60, Cl, 13.14).

EXAMPLE 4

2-(p-Chlorobenzyl)-3-[p-(2-morpholinoethoxy)phenyl-6-methoxybenzo[b]furan (4)

(a) n-Butyl lithium (1.41 ml of a 1.56M solution, 2.2 mmol) was added dropwise to a solution of 4-[2-morpholinoethoxy]phenyl bromide (630 mg, 2.2 mmol) in THF (5 ml) at −78° C. After stirring for 30 minutes at −78° C., 2-(p-chlorobenzyl)-6-methoxy-3(2H)-benzofuranone (613 mg, 2.0 mmol) in THF (2 ml) was added dropwise to the mixture at −78° C. The reaction mixture was allowed to warm to room temperature. After stirring for 18 hours, it was quenched with saturated ammonium chloride, THF was evaporated off to yield an oil which was dehydrated with concentrated hydrochloric acid (2 ml) in ethanol (10 ml). The mixture was refluxed for 2 hours, whereupon ethanol was removed. It was then basified with 10% sodium hydroxide (20 ml) and extracted with dichloromethane (3×40 ml).

The dichloromethane extract was washed with water (3×20 ml), dried (anhydrous sodium sulphate) and the solvent was evaporated off to give a solid which was chromatographed on silica gel. Elution with (dichromethane:hexane:triethylamine=1:2:0.3), yielded a colourless solid of the free base. (50 ml) and cooled to 0° C. Dry hydrogen chloride gas was bubbled for 10 minutes. The hydrochloride salt of the title compound, which preciptated out was filtered off at the pump, rinsed with ether, and recrystallised from isopropanol. Yield (19 %); m.p. 213°–214° C.; $^1$H-NMR (CDCl$_3$) δ2.51–2.65 (m, 4H, N(CH$_2$CH$_2$)$_2$O), 2.84 (t, 2H, J6.0 Hz, OCH$_2$CH$_2$N), 3.68–3.80 (m, 4H, N(CH$_2$CH$_2$)$_2$O), 3.83 (s, 3H, OCH$_3$), 4.11 (distorted t, 4H, J 6.0 Hz, OCH$_2$CH$_2$N, CH$_2$ at C-2), 6.72–7.46 (m, 11H, ArH ); m/z (%) 479 (M$^+$−HCl, 10), 477 (M$^+$−HCl, 27), 368 (28), 288 (80), 100 (100). (Found: C, 65.52, H, 5.69, N, 2.55, Cl, 12.95. C$_{28}$H$_{28}$ClNO$_4$.HCl required C, 65.37, H, 5.68, N, 2.72, Cl, 13.78).

(b) Magnesium bromide etherate (0.194 g, 0.75 mmol) was dissolved in 20 ml ether in a two-necked flask under oxygen-free nitrogen atmosphere at room temperature. After stirring for 1 hour, 2-(p-chlorophenylmethylene)-3-[p-(2-morpholinoethoxy)phenyl]-6-methoxy-2,3-dihydrobenzo[b]furan-3-ol (5) (0.247 g, 0.5 mmol) in ether (10ml) was added dropwise to the mixture. After stirring for 4 hours, LiAlH$_4$ (0.076 g, 2.0 mmol) was added to the above reaction mixture. The reaction mixture was left overnight at room temperature. After stirring overnight, ethyl acetate was added dropwise till hydrogen evolution ceased. The above mixture was washed with water followed by brine (2×20 ml), dried (anhydrous magnesium sulfate) and the solvent was evaporated off to give an oil which was chromatographed on silica. Elution with (chloroform:hexane:triethylamine=1:1:0.2) yielded a white solid of the free base (R$_f$=0.4). Yield (60%); m.p. 126°–128° C.; $^1$H-NMR (CDCl$_3$)(15) 2.60–2.63 (m, 4H, N(CH$_2$CH$_2$)$_2$0(ring)), 2.85 (t, 2H, OCH$_2$CH$_2$N), 3.74–3.77 (m, 4H, N(CH$_2$CH$_2$)$_2$O(ring)), 3.84 (s, 3H, OCH$_3$), 4.11 (CH$_2$ at C-2), 4.17 (t, 2H, OCH$_2$CH$_2$N), 6.84–7.44 (m, 11H, ArH); m/z (%) 479(10), 491(35), 100(100).

EXAMPLE 5

2-(p-Chorophenylmethylene)-3-[p-(2-morpholinoethoxy)phenyl]-6-methoxy-2,3-dihydrobenzo[b]furan-3-ol (5)

n-Butyl lithium (2.87 mi of a 1.28M solution, 3.68 mmol) was added dropwise to a solution of 4-[2-morpholinoethoxy]phenyl bromide (0.80 ml, 3.68 mmol) in THF (10 ml) at −78° C. under nitrogen atmosphere. After stirring for 1 hour at −78° C., 2-(p-chlorobenzylidene)-6-methoxy-3(2H)-benzofuranone (1.0 g, 3.50 mmol) in THF ( 5 m was added dropwise to the mixture at −78° C. The reaction mixture was left overnight at room temperature. It was quenched with saturated ammonium chloride, THF was evaporated off to yield an oil which was extracted with ethyl acetate (2×20 ml). The ethyl acetate extract was washed with water followed by brine (2×20 ml), dried (anhydrous magnesium sulfate) and the solvent was evaporated to give an oil which was chromatographed on silica gel. Elution with (chloroform:hexane:triethylamine=1:1:0.2) yielded a solid of the free base (R$_f$=0.3). Yield (56%); m.p. 69–70° C.; 1H-NMR (CDCl$_3$) δ 1.55 (brs, 1H, OH), 2.54–2.58 (m, 4H, N(CH$_2$CH$_2$)2O (ring)), 2.79 (t, 2H, OCH$_2$CH$_2$N), 3.7–3.74 (m, 4H, N(CH$_2$CH$_2$)$_2$ (ring)), 3.84 (3H, OCH$_3$), 4.09 (2H, OCH$_2$CH$_2$N), 5.64 (benzylidene proton), 6.72–7.60 (m, 11H, ArH). 13C-NMR δ(ppm) 104.4 (benzylidene carbon), 133.1 (C-2), 81.0 (C-3), 54.1 (OCH$_3$); IR (KBr) 1680 cm$^{-1}$ (C=C), 3400 cm$^{-1}$ (broad OH); m/z (%) 495(5), 493(10), 100(100). (Found: C, 68.14, H, 5.89, N, 2.75, Cl, 7.30. C$_{28}$H$_{28}$ClO$_5$N required C, 68.15, It, 5.68, N, 2.84, Cl, 7.10).

EXAMPLE 6

2-(p-Fluorobenzyl)-3-[p-(2-diethylaminoethoxy)-phenyl]-6-methoxybenzyl[b]furan(6)

The method of example 5 followed by example 4b was used for the preparation of 2-(p-fluorobenzyl)-3-[p-(2-diethylaminoethoxy)phenyl]-6-methoxybdnzo[b]furan. The specific gram proportions of reactants used are similar and are not meant to be limiting and can be varied around idealised stoichiometric proportion in the usual way known to those skilled in the art.

Yield (52%); m.p. 146°–147° C. (Found: C, 67.05, H, 6.36, N, 2.77, F, 3.79. C$_{28}$H$_{30}$FNO$_3$.HCl.H$_2$O required C, 67.07, H, 6.59, N, 2.79, F, 3.79).

EXAMPLE 7

2-(p-Fluorobenzyl)-3-[p-(2-pyrrolidinoethoxy)phenyl]-6-methoxybenzo[b]furan(7)

The method of example 5 followed by example 4b was used for the preparation of 2-(p-fluorobenzyl)-3-[p-(2-pyrrolidinoethoxy)phenyl]-6-methoxybenzo[b]furan.

Yield (54 %); m.p. 178°–179° C. (Found: C, 68.61, H, 6.06, N, 3.24, F, 4.07. C$_{28}$H$_{28}$FNO$_3$.HCl.5H$_2$O required C, 68.57, H, 6.12, N, 2.86, F, 3.86).

EXAMPLE 8

2-(p-Fluorobenzyl)-3-[p-(2-piperidinoethoxy)phenyl]-6-methoxybenzo[b]furan(8)

The method of example 5 followed by example 4b was used for the preparation of 2-(p-fluorobenzyl )-3-[p-(2-piperidinoethoxy)phenyl]-6-methoxybenzo[b]furan.

Yield (59 %); m.p. 154°–156° C. (Found: C, 68.18, H, 6.39, N, 2.88, F, 4.00. C$_{29}$H$_{30}$FNO$_3$.HCl.H$_2$O required C, 67.84, H, 6.43, N, 2.73, F, 3.70).

EXAMPLE 9

2-(p-Fluorobenzyl)-3-[p-(2-morpholinoethoxy)phenyl]-6-methoxybenzo[b]furan (9)

The method of example 5 followed by example 4b was used for the preparation of 2-(p-fluorobenzyl)-3-[p-(2-morpholinoethoxy)phenyl]-6-methoxybenzo[b]furan.

Yield (60%); m.p. 105°–106° C. (Found: C, 72.94, H, 6.10, N, 2.99, F, 3.76. C$_{28}$H$_{28}$FNO$_4$ required C,72.89, H, 6.07, N,3.04, F, 4.12).

EXAMPLE 10

Ligand binding

The compounds of the invention have been tested for their ability to bind to:

(1) AEBS by competitive displacement of [3H]tamoxifen (321.9 GB 1/mmol)(New England Nuclear) from AEBS present in an established lymphoma cell line, EL4 which is deficient in estrogen receptor.

(2) ER by competitive displacement of [3H]estradiol (Amersham) (93.3 TBq/mmol) from ER present in an established human breast carcinoma-derived cell line, MCF7.

These studies document that each compound displaces [3H]tamoxifen from AEBS more effectively than tamoxifen itself (Table I) and that none binds appreciably to ER (Table II). These compounds as a class are therefore high-affinity and selective ligands for AEBS.

TABLE I

Competitive binding to antiestrogen-binding sites[a]

| Cpd No. | RBA[b] |
|---|---|
| 1a (Tamoxifen) | 100 |
| 1 | 391 ± 195 |
| 2 | 268 ± 92 |
| 3 | 605 ± 371 |
| 4 | 1828 ± 446 |

[a] Determined by competitive ligand binding assays using EL4 whole cells as the source of AEBS. Cells were incubated with 5 nM [$^3$H]tamoxifen in the absence or presence of an increasing molar excess of unlabelled competing ligand (50 nM–1000 nM). The binding reaction was performed and bound [$^3$H]tamoxifen quantitated as described in the experimental section.

[b] RBA, relative binding affinity = $\dfrac{RBA_{50} \text{ of 1a}}{RBA_{50} \text{ of test compound}} \times 100$ where $RBA_{50}$ is the concentration required to reduce bound [$^3$H]tamoxifen by 50% of the control value (obtained in the absence of competing ligand). The data are the mean ± SEM of two experiments.

TABLE II

Competitive binding to the estrogen receptor[a]

| Cpd No. | Bound [$^3$H]estradiol[b] (% of control) |
|---|---|
| 1a (Tamoxifen) | 82.0 ± 2.0 |
| DES[c] | 123 ± 3.5 |
| 1 | 98.0 ± 1.0 |
| 2 | 993 ± 3.5 |
| 3 | 93.5 ± 0.5 |
| 4 | 103.5 ± 2.5 |

[a] Determined by competitive ligand binding assays using MCF7 whole cells as the receptor source. Cells were incubated with 5 nM [$^3$H]estradiol in the absence or presence of a hundred-fold excess of DES or each test compound. The binding reaction was performed and bound [$^3$H]estradiol quantitated as described in the experimental section.

[b] Bound [$^3$H]estradiol in the absence of unlabelled competing ligand was set at 100%. The data are the mean ± SEM of two experiments.

[c] DES = diethylstilbestrol

EXAMPLE 11

Antiproliferative activity

Cell lines: EL4 and MCF7 were propagated in HEPES-buffered RPMI 1640 medium which was rendered lipoprotein-poor for EL4 cells alone. RTx6, an AEBS-deficient variant of the MCF7 cell line (Faye et al., *Proc. Natl.Acad. Sc.U.S.A.* (1983), 80:3158–3162), was propagated in identical manner as MCF7 except that $10^{-5}$M tamoxifen was continuously present in the growth medium until 24 hours before use.

[$^3$H]Thymidine incorporation: EL4 cells in the logarithmic growth phase were inoculated into duplicate wells of a 96-well plate at a density of 106 cells/ml (0.18 ml/well). Tamoxifen and test compounds dissolved in ethanol were added (0.02 ml/well) after appropriate dilutions from 1 mM stock solutions to yield final concentrations between $10^{-8}$M to $10^{-6}$M. Control wells received an identical concentration of solvent alone. After 48 hours, each well was pulsed with [$^3$H]thymidine (New England Nuclear)(74 KBq/well, 0.02 ml/well) for 60 minutes. Macromolecular incorporation of [$^3$H]thymidine was quantitated by harvesting cells on a Brandel harvester fitted with scintillant-coated glass microfibre filters (Ready Filters, Beckman). Filters were washed sequentially with isotonic sodium chloride, 10% (w/v) trichloroacetic acid and 95% ethanol, oven dried and counted.

[$^3$H]Thymidine incorporation by MCF7 and RTx6 cells was determined by the same technique with the following modifications: (i) cells were plated at 4,500 cells/well (0.18 ml/well); (ii) compounds and [$^3$H]thymidine (37 KBq/well, 0.02 ml/well) were added 24 hours after plating; (iii) cells were trypsinized (0.05 ml of 0.05%/0.53 mM EDTA/well) prior to harvesting. $IC_{50}$ is the concentration of a compound required to reduce [$^3$H]thymidine incorporation to 50% of the control value.

Cell counts were performed manually using a Neubauer hemocytometer. Cell viability was assessed by trypan blue exclusion. The table below (Table HI) is a summary

TABLE III

Antiproliferative effect of benzofurans[a]

| Cpd No. | $IC_{50}$ (nM)[b] EL4 | $IC_{50}$ (nM)[b] MCF7 |
|---|---|---|
| 1a (Tamoxifen) | 535 ± 285 | 7200 ± 800 |
| 1 | 950 ± 50 | 5025 ± 25 |
| 2 | 475 ± 225 | 2300 ± 100 |
| 3 | 300 ± 150 | 2050 ± 50 |
| 4 | 335 ± 145 | 6500 ± 500 |

[a] Measured as inhibition of [$^3$H]thymidine incorporation by EL4 and MCF7 cells as described in the experimental section.

[b] $IC_{50}$ is the concentration of a compound required to reduce [$^3$H]thymidine incorporation to 50% of its control (untreated) value. The data are the mean ± SEM of two experiments.

of several experiments showing that all compounds were more effective than tamoxifen in inhibiting DNA synthesis in MCF7 cells and that all compounds, except compound 1, were also more effective than tamoxifen in EL4 cells. Decreases in cell density were temporally associated with inhibition of [$^3$H]thymidine incorporation in both cell lines (FIG. 1 ).

With the exception of compound 4, all compounds of the invention were less effective in decreasing DNA synthesis by RTx6 cells than by MCF7 cells (FIG. 2).

EXAMPLE 12

Cholesterol biosynthesis

De novo synthesis of cholesterol by EL4 cells from [$^3$H]acetic acid, sodium salt (Amersham) (103 GBq/mmol) was quantitated using [4-$^{14}$C]cholesterol (Amersham) (2.04 GBq/mmol) as internal standard by the method of Ho et al., *J.Exp.Med.*(1977) 145:1531–1549). Each determination was performed in triplicate, each consisting of 0.8 ml of a cell suspension ($2 \times 10^7$ EL4 cells/ml) incubated with [$^3$H]acetate (0.25 mM) and the test compound (0.1 ml, $10^{-6}$M–$10^{-4}$M) for 5 or 48 hours at 37° C.

Table IV shows significant inhibition of cholesterol biosynthesis by compound 2 as early as 5 hours after treatment. This was not associated with loss of cell viability implying that the effect on cholesterol biosynthesis preceded events which subsequently led to cell killing. Compound 4 at higher concentration (Table V) also decreased incorporation of [$^3$H]acetate into cholesterol.

EXAMPLE 13

Pharmaceutical Composition

Following the procedure of Example 3 of U.S. Pat. No. 4,536,516(ICI), 50 parts of 2-(p-chlorobenzyl)-3-[p-(2-morpholinoethoxy)]-6-methoxybenzo[b]furan, 42 parts of maize starch and 7 parts of alginic acid are intimately mixed and granulated using 10% maize starch paste as the granulating agent. The granules are dried at a temperature not exceeding 50° C., and then mixed with 1 part of magnesium stearate. The mixture was compressed into tablets each weighing 50 mg which are thus suitable for oral administration for therapeutic purposes.

TABLE IV

Effect of compound 2 on cholesterol biosynthesis by EL4 cells

| Compound | % total radioactivity incorporated as cholesterol[c] | | | % inhibition of cholesterol synthesis | % cell viability[e] |
|---|---|---|---|---|---|
| | I[f] | II[f] | Mean | | |
| Control[a] | 0.20 | 0.22 | 0.23 ± 0.02 | — | 96 |
| | 0.25 | 0.23 | | | |
| | 0.26 | 0.24 | | | |
| 2[a] | 0.13 | 0.11 | 0.12 ± 0.01 | 48 | 91 |
| | 0.10 | 0.12 | | ($p < 0.01$)[d] | |
| | 0.12 | 0.14 | | | |
| Control[b] | 0.34 | 0.28 | 0.32 ± 0.02 | — | 92 |
| | 0.32 | 0.30 | | | |
| | 0.36 | 0.32 | | | |
| 2[b] | 0.16 | 0.14 | 0.17 ± 0.02 | 47 | 87 |
| | 0.15 | 0.17 | | ($p < 0.01$)[d] | |
| | 0.24 | 0.14 | | | |

[a] EL4 cells (20 × 10$^6$ cells/ml in well) were incubated with 0.25 mM [$^3$H]acetate in the absence or presence of 2 (10$^{-6}$M) for 5 hours.
[b] EL4 cells (20 × 10$^6$ cells/ml in well) were incubated with 0.25 mM [$^3$H]acetate in the absence or presence of 2 (10$^{-7}$M) for 48 hours.
[c] $\frac{\text{Radioactivity incorporated as cholesterol}}{\text{Total radioactivity incorporated by cells}} \times 100$
[d] p value was obtained by applying Student's t-test.
[e] Cell viability was estimated by trypan blue exclusion.
[f] Data from two experiments (each performed in triplicate)

TABLE V

Effect of compound 4 on cholesterol biosynthesis by EL4 cells

| Compound | % total radioactivity incorporated as cholesterol[b] | | | % inhibition of cholesterol synthesis | % cell viability[d] |
|---|---|---|---|---|---|
| | I[e] | II[e] | Mean | | |
| Control[a] | 0.25 | 0.24 | 0.25 ± 0.02 | — | 96 |
| | 0.24 | 0.27 | | | |
| | 0.20 | 0.28 | | | |
| 4[a] | 0.19 | 0.11 | 0.11 ± 0.03 | 56 | 79 |
| | 0.09 | 0.12 | | ($p < 0.05$)[c] | |
| | 0.05 | 0.11 | | | |

[a] EL4 cells (20 × 10$^6$ cells/ml in well) were incubated with 0.25 mM [$^3$H]acetate in the absence or presence of 4 (10$^{-4}$M) for 5 hours.
[b] $\frac{\text{Radioactivity incorporated as cholesterol}}{\text{Total radioactivity incorporated by cells}} \times 100$
[c] p value was obtained by applying Student's t-test.
[d] Cell viability was estimated by trypan blue exclusion.
[e] Data from two experiments (each performed in triplicate)

What we claim is:

1. 2-(Benzyl)-3-arylbenzo[b]furan in free base form and pharmaceutically acceptable acid-addition salts thereof, of formula (1

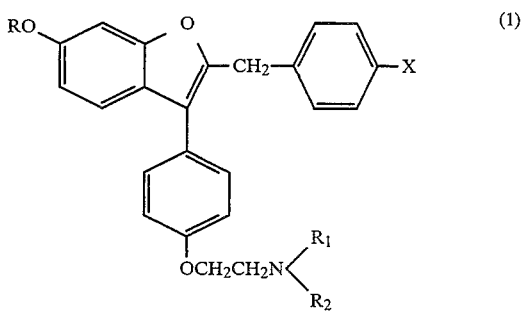

where
R represents H, or methyl group,
R$_1$, R$_2$ are identical or different and represent C$_{1-2}$ alkyl or R$_1$ and R$_2$ together with the nitrogen atom to which they are attached represent a saturated heterocyclic group, and their pharmaceutically acceptable acid addition salts and X represents bromo, chloro, fluoro or hydrogen.

2. 2-(Benzyl)-3-arylbenzo[b]furan according to claim 1, wherein said C$_{1-2}$ alkyl is independently methyl or ethyl, or R$_1$ and R$_2$ together with the nitrogen to which they are attached represent a pyrrolidino, piperidino or morpholino group.

3. 2-(P-Chlorobenzyl)-3-[p-(2-dimethylaminoethoxy)phenyl]-6-methoxy-benzo[b]furan.

4. 2-(p-Chlorobenzyl )-3-[p-(2-pyrrolidinoethoxy)-phenyl ]-6-methoxy-benzo [b]furan.

5. 2-(P-Chlorobenzyl)-3-[p-(2-piperidinoethoxy)-phenyl]-6-methoxy-benzo[b]furan.

6. 2-(p-Chlorobenzyl)-3-[p-(2-morpholinoethoxy)-phenyl]-6-methoxy-benzo[b]furan.

7. 2-(p-Fluorobenzyl )-3-[p-( 2-dimethylaminoethoxy)phenyl]-6-methoxy-benzo[b]furan.

8. 2 - ( p-Fluorobenzyl ) - 3 - [p- ( 2 -pyrrolidinoethoxy)phenyl]-6-methoxy-benzo [b]furan.

9. 2-(p-Fluorobenzyl)-3-[p-(2-piperidinoethoxy)-phenyl]-6-methoxy-benzo[b]furan.

10. 2-(p-Fluorobenzyl)-3-[p-(2-morpholinoethoxy)-phenyl]-6-methoxy-benzo[b]furan.

* * * * *